United States Patent
Neugebauer et al.

(10) Patent No.: US 8,247,636 B2
(45) Date of Patent: Aug. 21, 2012

(54) FASTENING TAPE FOR A HYGIENE ITEM, AND METHOD FOR PRODUCING A FASTENING TAPE FOR A HYGIENE ITEM

(75) Inventors: Robert Neugebauer, Neunkirchen (DE); Christian Felkl, Breitengüssbach (DE)

(73) Assignee: Koester GmbH & Co. KG, Altendorf (DE)

( * ) Notice: Subject to any disclaimer, the term of this patent is extended or adjusted under 35 U.S.C. 154(b) by 352 days.

(21) Appl. No.: 10/589,633

(22) PCT Filed: Feb. 18, 2005

(86) PCT No.: PCT/DE2005/000276
§ 371 (c)(1), (2), (4) Date: Nov. 1, 2006

(87) PCT Pub. No.: WO2005/077314
PCT Pub. Date: Aug. 25, 2005

(65) Prior Publication Data
US 2007/0197995 A1    Aug. 23, 2007

(30) Foreign Application Priority Data

Feb. 18, 2004 (DE) .......................... 10 2004 008 283

(51) Int. Cl.
*A61F 13/15* (2006.01)
*A61F 13/20* (2006.01)

(52) U.S. Cl. ........ 604/358; 604/389; 604/390; 604/391; 604/392; 2/908; 2/912; 2/920; 24/306

(58) Field of Classification Search .................. 604/358, 604/389–392; 2/906–920; 24/306
See application file for complete search history.

(56) References Cited

U.S. PATENT DOCUMENTS

| | | | | |
|---|---|---|---|---|
| 4,063,559 A * | 12/1977 | Tritsch | | 604/390 |
| 4,237,889 A * | 12/1980 | Gobran | | 604/389 |
| 4,568,344 A * | 2/1986 | Suzuki et al. | | 604/389 |
| 5,019,073 A * | 5/1991 | Roessler et al. | | 604/391 |
| 5,288,546 A * | 2/1994 | Roessler et al. | | 428/40.1 |
| 5,399,219 A * | 3/1995 | Roessler et al. | | 156/259 |
| 5,605,735 A * | 2/1997 | Zehner et al. | | 428/100 |
| 5,624,429 A | 4/1997 | Long et al. | | |
| 6,210,389 B1 | 4/2001 | Long et al. | | |
| 6,276,032 B1 * | 8/2001 | Nortman et al. | | 24/572.1 |
| 7,189,220 B2 * | 3/2007 | Miyoshi et al. | | 604/389 |
| 2003/0009144 A1 * | 1/2003 | Tanzer et al. | | 604/391 |

FOREIGN PATENT DOCUMENTS

| | | | |
|---|---|---|---|
| DE | 83 27 230 | | 1/1984 |
| EP | 0 840 585 | | 5/1998 |
| EP | 0 983 760 | | 3/2000 |
| GB | 2284742 A | * | 6/1995 |
| JP | 63-309606 | | 12/1988 |
| WO | WO 97/32555 | | 9/1997 |

OTHER PUBLICATIONS

International Search Report.

* cited by examiner

*Primary Examiner* — Tatyana Zalukaeva
*Assistant Examiner* — Ginger T Chapman
(74) *Attorney, Agent, or Firm* — Collard & Roe, P.C.

(57) ABSTRACT

To ensure an excellent slip-proof effect for a hygiene item, in particular for a baby diaper or an incontinence diaper when opening the diaper, a fastening tape is proposed having a separate film-like grip area with a macroscopically structured surface. Likewise, a hygiene item having such a grip area and a method for manufacturing such a fastening tape are proposed.

17 Claims, 5 Drawing Sheets

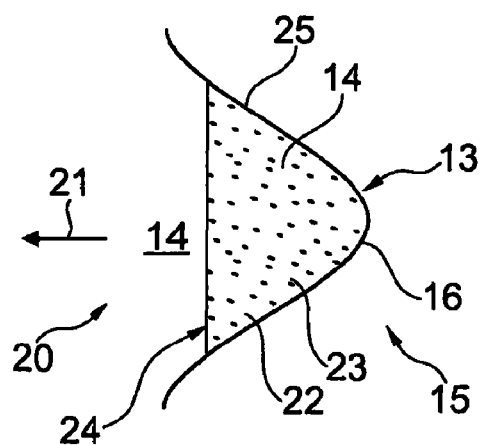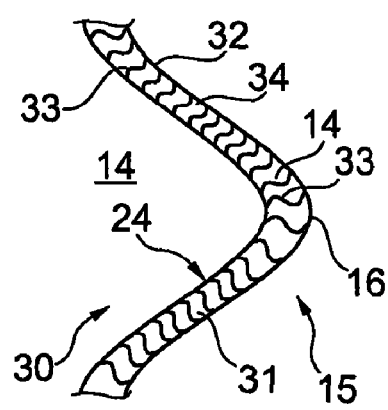
Fig. 6a  Fig. 6b
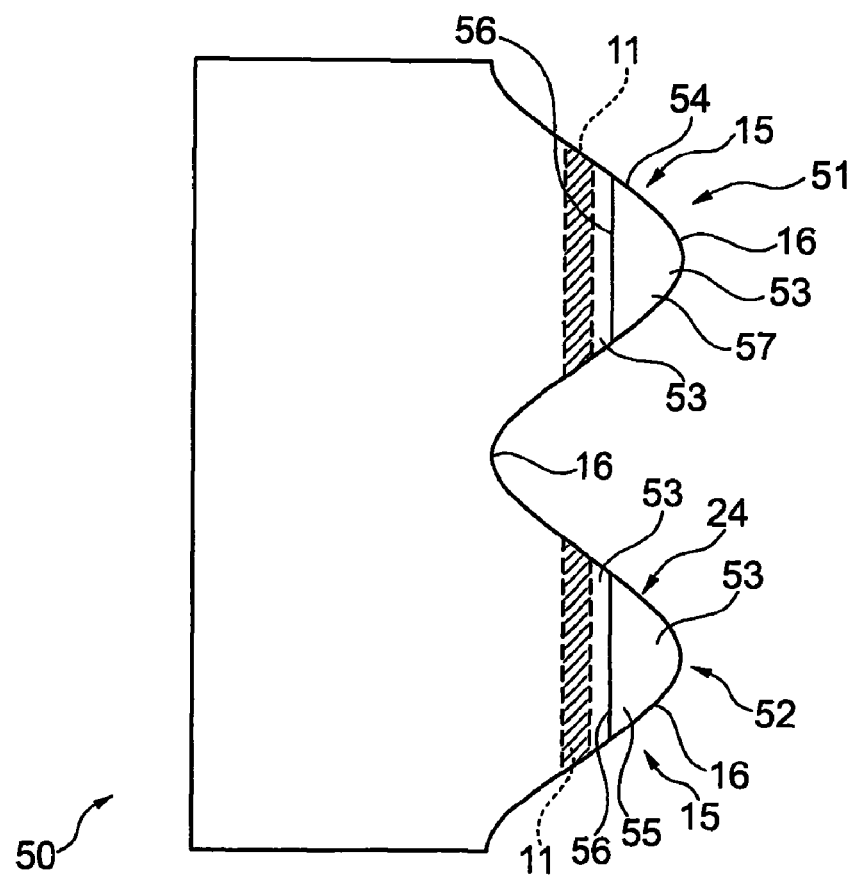
Fig. 6d

FASTENING TAPE FOR A HYGIENE ITEM, AND METHOD FOR PRODUCING A FASTENING TAPE FOR A HYGIENE ITEM

CROSS REFERENCE TO RELATED APPLICATIONS

Applicants claim priority under 35 U.S.C. §119 of German Application No. 10 2004 008 283.9 filed Feb. 18, 2004. Applicants also claim priority under 35 U.S.C. §365 of PCT/DE2005/000276 filed Feb. 18, 2005. The international application under PCT article 21(2) was not published in English.

BACKGROUND OF THE INVENTION

1. Field of the Invention The invention relates to a fastening tape for a hygiene item, said hygiene item and a method for producing a fastening tape for a hygiene item. In particular, the invention relates to a fastening tape for a baby diaper or for an incontinency diaper, said baby diaper or incontinency diaper and a method for producing such diapers.

2. Description of the Prior Art Opening the fastening tape on a diaper to put the diaper on or take it off, involves gripping an end of the fastening tape using one's fingers and pulling the fastening tape away from the surface of the diaper that cooperates with the tape or away from a release tape on the surface of the diaper. As a result, a fastening tape often has a protruding section which extends as the "free end" beyond the closing area of the tape. EP 0 840 585 B1 discloses that for fastening tapes with a closing area and a protruding section it is especially favorable from a manufacturing standpoint to make a wavy cut along the machine transport direction to sever the strips of tape during production. The wavy cut results in a tape having a wavy end with a plurality of wavy heads, with a protruding section being formed on each wavy head on the wavy end of the tape.

Before the initial use in particular, the diaper fastening tapes are affixed very securely to the diaper or to a similar surface due to the manufacturing process. Diapers can also be closed relatively securely, in particular in the case of incontinency diapers. Then the user's fingertips can easily slip away from the protruding sections gripped by the fingers. To avoid this, the fingers must be pressed relatively tightly against the protruding tape to be able to reliably grip the diaper fastening tape and/or be able to open the diaper reliably.

To improve security in gripping the protruding sections, numerous attempts have been made so far. For example, Japanese Patent Application JP 62-142825 (Patent No. JP 8-2365) has proposed that an edge of the protruding section should be folded over. Additionally or alternatively, a small line of glue may be provided there. In similar approaches, heat seal adhesive surfaces applied by nozzles on the protruding section have also been proposed.

According to other proposals, a hook material of the closing area is also applied to the edge of the fastening tape. According to U.S. Pat. No. 6,210,389, a continuous hook surface is provided from the closing area to the end of the tape whose hooks are thermally and mechanically flattened toward the edge or are cut flat toward the edge to permit more reliable haptic feedback in gripping the tape. However, according to U.S. Pat. No. 5,624,429, the same or similar hooks are provided on the protruding section as in the closing area or the cut-off stumps thereof, whereby a lower density of hooks per unit of area should be provided in the protruding area. In both cases, the respective hooks are arranged on a single backing surface and/or film.

SUMMARY OF THE INVENTION

The object of the present invention is to provide a fastening tape which offers excellent slip prevention to prevent the user's fingers from slipping off the diaper fastening tape even under adverse use conditions and does so with a very good cost-benefit ratio and can also be adapted flexibly in production to meet customer wishes.

This object is achieved according to one aspect of the present invention by a fastening tape for a hygiene item, in particular for a baby diaper or an incontinence diaper, having a fastening area for permanent fastening to a hygiene item and with a closing area for simultaneous detachable fastening to a surface of the hygiene item, whereby the fastening tape has a protruding section between the closing area and an end of the tape to be assigned to the closing area and the protruding section has a separate foam-like gripping area with a macroscopically structured surface.

By way of explanation of terms, it should be pointed out that the closing area has in particular a plurality of hooks, e.g., more than 100 hooks. A closing area provided with hooks may function advantageously as a component of a two-component fastening system, in particular a hook-and-loop-type fastening system. All surfaces capable of working together are suitable in this sense, wherein arrangements of one component protruding out of one surface are able to grip behind recesses, loops, openings, fibers or the like in the other component, so that the result is a force resisting separation of the two surfaces from one another. In addition to hooks, numerous other shapes including mushroom-head-shaped rods or similar forms may also be used for the protruding arrangements on the one component.

The fastening area of the diaper fastening tape serves to fasten it permanently to a surface, e.g., on the wings of a diaper. This results in a free end of the tape, the so-called user end, on the opposite end. The closing area is arranged in proximity thereto and serves to guide the diaper after being applied by the user to a surface cooperating with the closing end, usually on the opposite wing of the diaper and/or on the abdominal side of the applied diaper, and to close the diaper in a reopenable manner. To do so, the diaper fastening tape may be gripped by the protruding section in particular, i.e., the section situated on the user end of the tape on the unfastened side of the closing area.

A diaper fastening tape usually extends in a longitudinal direction from the fastening area to the protruding section. A diaper fastening tape is often rectangular or at least essentially rectangular in shape.

In comparison with those known in the past, the aspect of the present invention presented here represents a greatly improved cost-benefit compromise. In comparison with a continuous hook material all the way to the edge of the fastening tape or a plastic base extending all the way to the edge, the grip area can easily be changed during the course of production on the machine. The grip area may in this way be rapidly and inexpensively adapted to customer wishes. This advantage is achieved by the fact that the grip area is designed separately, i.e., is designed separately from the neighboring structural groups of the diaper fastening tape, in particular the closing area, for example, and/or has other structural components materially.

The present invention achieves the inexpensive means of providing a slip-proof grip according to the aspect presented here by the fact that it proposes a "macroscopically structured surface" for the separate grip area. The grip area should preferably be arranged on the tape in such a way that it is definitely elevated above the surface, preferably exactly by the amount of its own thickness, i.e., by the thickness of a corresponding design element. The actual grip area is then situated on the surface of the structurally separate design element facing away from the tape. A macroscopic structure is to be provided on this surface, i.e., in particular the structure can be touched with one finger. The advantage of such a relatively large dimensional structure is, among other things, the fact that the fingers get a secure grip on the protruding section and thus on the user end of the diaper fastening tape even under adverse circumstances. Adverse circumstances may occur in particular when the user end of the fastening tape or the fingers of the user are moist, wet or soiled. Especially when applying baby diapers, this possibility often cannot be ruled out. To this extent the proposed macroscopic surface structure is especially advantageous in comparison with an adhesive tape as proposed in JP 8-2365.

In comparison with a laminated film or a hot-melt adhesive layer, the macroscopically structured surface yields a better grip. With regard to terminology, it should be explained here that a film has essentially a two-dimensional extent and is completely or at least mostly smooth on its surface on a macroscopic scale. On the other hand a structure designed or applied to a spot or surface improves the grip traction of the surface.

To this extent, the present invention offers the advantage over the hook surfaces of the closing areas designed as a grip area known from the state of the art, namely that the grip area according to the present invention can be designed easily and expensively to fulfill its task of having good grip traction. The enlarged hook area from the state of the art is disproportionately expensive. Likewise, reworking of this hook area is even more complex and expensive. In comparison with the film-like grip areas known from the state of the art, the present invention has the advantage that a much greater grip traction of the grip area can be achieved due to the macroscopically structured surface. In particular, the grip traction can be adapted relatively inexpensively to modified boundary conditions and/or to modified customer wishes.

In particular when the grip area is applied as an independent structural component separate from the actual diaper fastening tape, the grip area can be adapted quickly and inexpensively to customer wishes. Due to the fact that the grip area is produced by an independent component, the haptic properties of the grip area as well as the other mechanical properties can be adjusted, selected, adapted and/or revised in a targeted manner independently of the remainder of the diaper fastening tape. This can be readily accomplished in particular before application to the other diaper fastening tape and/or to a backing strip of the diaper fastening tape. On the other hand, this may of course also be accomplished after application.

In addition, it is also conceivable for the separate grip area to be formed by a structural component of the remainder of the diaper fastening tape, e.g., by a backing film of the diaper fastening tape. It should be noted here, however, that the functional unit adjacent to the protruding section and/or the grip area and/or the functional units of the diaper fastening tape adjacent to the protruding section and/or the grip area may be designed with a different structure so that the grip area is still designed separately.

In such an arrangement, it may be advantageous in particular to provide the macroscopic structure of the surface in the separate grip area only subsequently, in particular after bringing together the essential components of the diaper fastening tape, which may be accomplished by embossing in particular.

An especially inexpensive means of providing, applying and/or attaching the component for the grip area is achieved according to an especially preferred embodiment of this invention by the fact that the grip area is designed "like a film." In the present context the term "like a film" is understood to refer to a structural component, the area of which in $mm^2$ amounts to at least eight times the thickness in mm measured for this area. In the present case, such a component is then a film if it has sufficient inherent stability and is flexible. To obtain a film-like grip area, for example, a film piece may be glued or otherwise applied as a separate component to the protruding section, and this gluing or other application can be accomplished with little effort. Alternatively, a directly adhering material, e.g., a hot-melt adhesive or some other thermoplastic material such as TPE may be applied directly to the diaper fastening tape to be a film on the diaper fastening tape so that in turn an independent structured component on the diaper fastening tape is designed in the manner and with the properties of a film. In the case of hot-melt adhesives in particular, however, the component may be relatively brittle so that here it is better to speak of a film-like component. A film-like material for the structurally independent component forming the separate grip area is much more favorable in particular than a mechanically reworked hook material, as provided in U.S. Pat. No. 6,210, 389, for example, or more favorable than providing a few individually arranged hooks or hook spots as proposed in U.S. Pat. No. 5,624,429. Therefore, the film-like material has no hooks.

In order for the grip area to be especially readily palpable and so that it can also be differentiated from a hook area arranged next to it, so that the grip area is of a different type of material than the hook area or closing area arranged next to it, it is proposed that it should have a structurally independent design element in the form of a film with a thickness of more than 100 μm, preferably less than 600 μm. Depending on the concrete type of macroscopic surface structure, no great mechanical requirements need be made of the separate film of the grip area. Therefore, even relatively thick films may be used with little expenditure of cost. Even if technically more demanding films are used, it may nevertheless be assumed that the proposed approach will remain quite inexpensive. In particular, aftertreatment steps, such as those required in U.S. Pat. No. 6,210,389 B1, for example, may be omitted.

The structured surface may in particular have an embossing which imparts an improved haptic property. Embossing causes a tangible increase in the slip-proof property at low cost. As an alternative or additionally to the embossing, the grip area may also have an edge which drops toward a backing strip or the like and acts like the embossing from a haptic standpoint so as to form in this way a macroscopically structured surface. In the latter case in particular, macroscopic structuring of the other surface of the grip area may be omitted.

The grip area may intentionally be adjusted to be isotropic or anisotropic in its strain properties and bending properties if the embossing has a plurality of straight and curved lines, a few of which are preferably joined together. When gripping the grip area with the finger, these may also very pleasantly offer preferred gripping areas as clusters of embossing. Lines grouped in this way may form alphabet letters and/or numbers in particular.

The grip area may be arranged on a grip edge of the protruding section, whereby the grip area may be designed in strips, for example, and may run in its form at least partially essentially according to the grip edge. For example, it may be geometrically similar to the grip edge of the protruding section, it may run along the edge of the strip or it may be arranged at a distance from the edge of the strip. The grip area may also be designed in the form of a circle or ring. The number, size and shape are subject to only a few restrictions. In particular, numerous basic geometric shapes or combinations thereof and inscriptions or graphic displays may be used for the shape of the grip area. The grip area may also be in several grip area islands all of which are preferably arranged within the protruding section. In particular when the grip area runs along the edge of the protruding section but not limited to this case, it may be advantageous for the grip area to follow a meandering pattern.

If the grip area is arranged on the grip edge or at least close to the strip edge, it can usually be perceived best by the fingertips. The same thing is also true if the grip area is designed to be geometrically similar to or at least approximated to the shape of the grip edge. In the case of an offset between the grip area and the edge of the strip, however, the grip area is usually visually more discernible. The same thing is also true when the grip area has a distinctly different geometry from the edge area of the protruding section.

The grip area is especially easy to locate both haptically and visually if it is at the same distance from the closing area as from the end of the strip assigned to the closing area.

The separate film-like grip area with the macroscopically structured surface may be arranged on one side of the fastening tape or on both sides of the fastening tape. If such a grip area is provided on only one side of the fastening tape, this may be on the side of the strip where the closing area is also arranged. In this case, it would cause the thumb of the user's hand to stop during the usual use. If a grip area is arranged on the side that is free of the closing area, i.e., on the opposite side of a backing strip carrying the closing area, then the grouped fingers of the user's hand will tend to come to a rest there. Accordingly, it is also proposed that the film-like grip area with the macroscopically structured surface on the side of the strip carrying the closing area should be completely next to the latter.

Alternatively or additionally, the separate grip area may also be situated on the opposite side, preferably also completely next to the closing area. However, a part of the grip area on this side or an additional island of the grip area may also be situated below the closing area. This offers a greater gripping surface for the grouped fingers of the user's hand in particular. With regard to terminology, it should be explained that the grip area is arranged completely next to the closing area in the sense of the present patent application if, in a projection of the closing area and the grip area onto a plane parallel to the diaper fastening tape does not result in any overlapping, preferably not even any direct abutment.

In a preferred embodiment with separate film-like grip areas on both sides of the fastening tape, at least a first grip area and a second grip area on different sides of the strip are of the same size and arranged so they cover one another. Therefore, the protruding section feels very stable. Such a constellation as well as the other features mentioned above can be achieved even if the protruding section has a separate film-like grip area with a macroscopically structured surface, whereby the separate film of the grip area is arranged on both sides of the fastening tape. In particular, it may reach around the end of the fastening tape for this purpose.

It is self-evident that the arrangement of a grip area on the outside of the diaper fastening tape, in particular on the side which does not have the closing area, is also advantageous independently of the other features of the present invention to increase the stability of a roll which is then cut crosswise to produce the diaper fastening tape. The material of the grip area may preferably be selected so that it ensures good haptic properties as well as ensuring good adhesion of a second layer of the role lying on the grip area. This grip area should also have a macroscopically structured surface and should preferably be designed as a film or like a film.

In addition, to further explain the terminology it should be pointed out that the protruding section may in particular be the entire section of the fastening tape protruding beyond the outermost closing means of the fastening tape to the edge of the fastening tape. The end of the band that is assigned to the closing area is understood to be the end of the band tape that is arranged closer to the closing area whereas it is closer to an opposing end of the strip of the fastening area of the fastening tape. It should be pointed out that the end of the strip is understood to refer to the end of the fastening tape extending longitudinally from the fastening area to the user end. The diaper fastening tape is an inseparable structure running beneath the closing area and through the grip area.

The protruding area is consequently usually free of the closing means. In the case of a diaper fastening tape according to WO 97/32555 A1 in which an additional closing means is provided on each diaper fastening tape, only the narrow strip is to be interpreted as the protruding area in addition to the additional fastener means. However, this cannot be generalized because of course a diaper fastening tape with a pronounced closing area and only isolated functionally practically inactive hooks in the actual protruding area is covered by the concept of the present invention. Thus, in concrete terms, such a diaper fastening tape in which a closing area and then a separate film-like gripping area having a macroscopically structured surface and finally a very few hooks that are functionally far less important than the closing area are arranged in the course from the fastening area to the user end.

According to a second aspect of the present invention, this object is also achieved by a hygiene item, in particular a baby diaper or an incontinence diaper which has a fastening tape having a separate film-like gripping area with a macroscopically structured surface on a protruding section.

Likewise, this object is achieved by a method for producing a fastening tape for a hygiene item of the aforementioned type in which method an embossed and/or otherwise macroscopically surface-structured film from a roll or a reel is laminated onto the protruding section of the closing strip. As an alternative to this, first a structurally independent structural component, such as a thermoplastic material, TPE and/or a hot-melt adhesive may be applied to the protruding section, e.g., by means of a nozzle, a spray mechanism, a roller or other suitable means. Additionally or alternatively, it is also possible to provide an area of the strip for providing a grip area with a macroscopic surface structure, which may happen with an embossing roll and/or an embossing wheel, for example. This may be accomplished preferentially before the applied material loses its shapeability after being applied so that it need not be heated again.

In this context, it should additionally be emphasized by way of explanation that the diaper fastening tapes are usually provided in their construction rolls, where these rolls are then cut into individual strips which are then applied as a first diaper fastening tape to a diaper. The considerations presented in this context with regard to the structure of the diaper fastening tapes and how they are produced equally also pertain to any rolls or reels as intermediate products from which the diaper fastening tapes can be removed, e.g., by cutting operations, such as transverse or longitudinal cutting, inasmuch as this is not explicitly negated elsewhere. Individual method steps may be performed directly on the diaper machine or at other points in time and/or on diaper fastening tapes that have already been separated, on reels or rolls and on intermediate products for the production of these reels or rolls.

BRIEF DESCRIPTION OF THE DRAWINGS

The invention will now be explained further below on the basis of various exemplary embodiments with reference to the drawing. Functionally identical components in the drawing may have the same reference numerals.

FIGS. 6a through 6e show various exemplary embodiments of the invention in detail according to the exemplary characterization detail area IV in FIG. 3. In addition to showing detail IV of FIG. 1 and a first wavy-head within detail area IV, FIG. 6d shows a second wavy-head that neighbors detail area IV that includes the first wavy head.

DETAILED DESCRIPTION OF THE PREFERRED EMBODIMENTS

Figure 1:
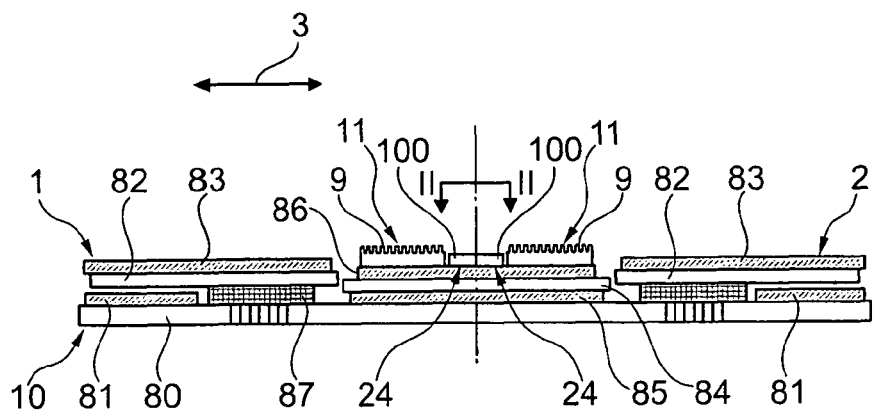
FIG. 1 shows schematically a cross section through two diaper fastening tape strips lying one above the other in the way in which they are transported and cut on a production machine.
Figure 2:
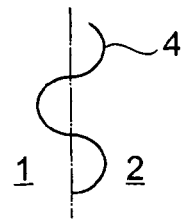
FIG. 2 shows schematically portions of the diaper fastening tape strips from FIG. 1, from the viewpoint II-II of FIG. 1, and a cutting line along which the diaper fastening tape strips from FIG. 1 are separated in production.
Figure 3:
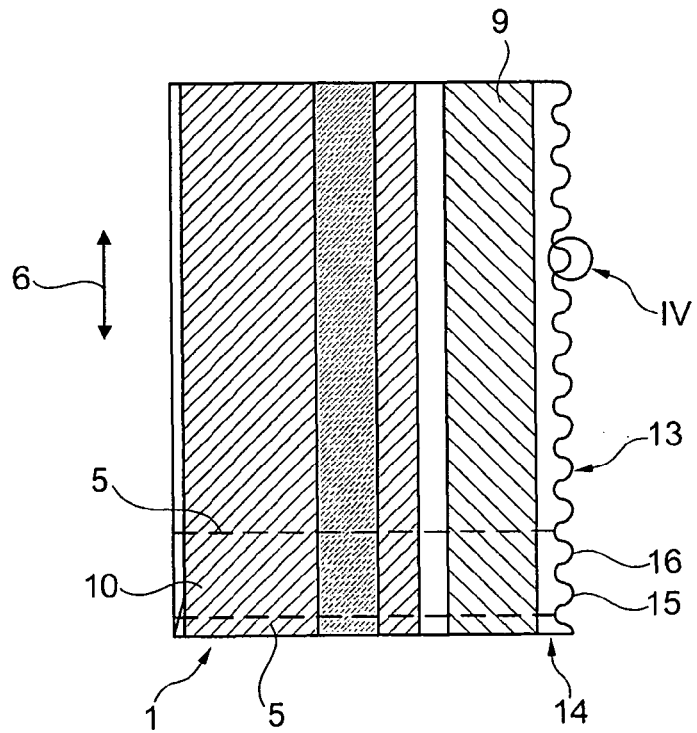
FIG. 3 shows schematically a top view of a diaper fastening tape strip after being separated from the opposing strip but before being cut to form the actual tape form, FIGS. 4 and 5 each show two diaper fastening tapes attached to a diaper

The two fastening tape strips 1 and 2 in FIG. 1 are joined at the ends in a machine cross-direction 3 and usually run in this form through the production machine which separates them, for example, in a wavy form (see FIG. 2) along a cut 4. FIG. 2 shows portions of fastening strips 1 and 2 of FIG. 1, as viewed from II-II in FIG. 1, along cut 4 with a wavy form. After being separated by the cut 4 in the machine cross-direction 3, the diaper fastening tape strip 1 is separated by separating cuts 5 (shown as an example in FIG. 3) to form individual diaper fastening tapes 10 which lie adjacent to one another in the machine direction 6 and can be taken from the machine.

Figure 4:
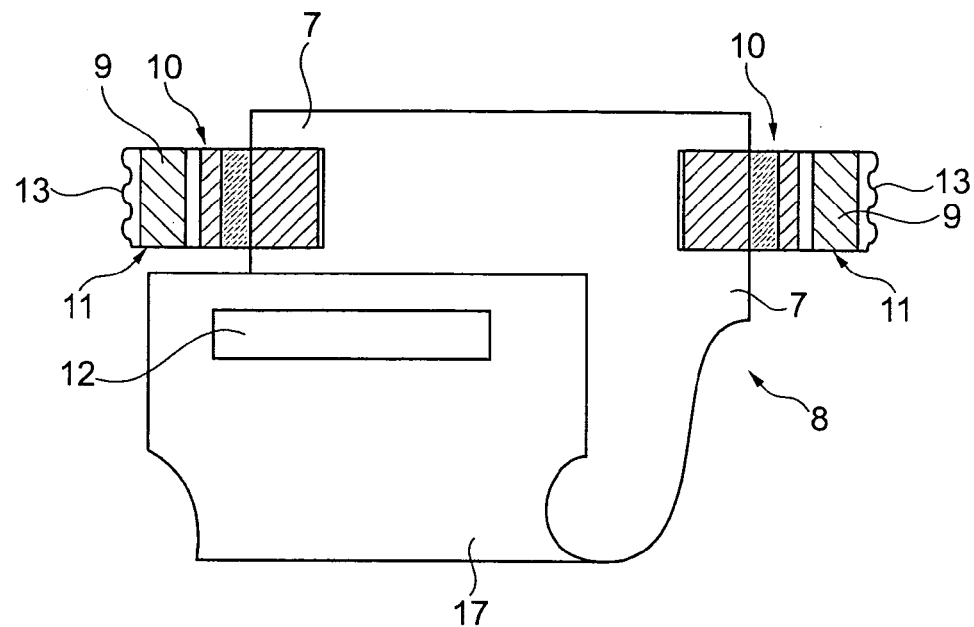
Figure 5:
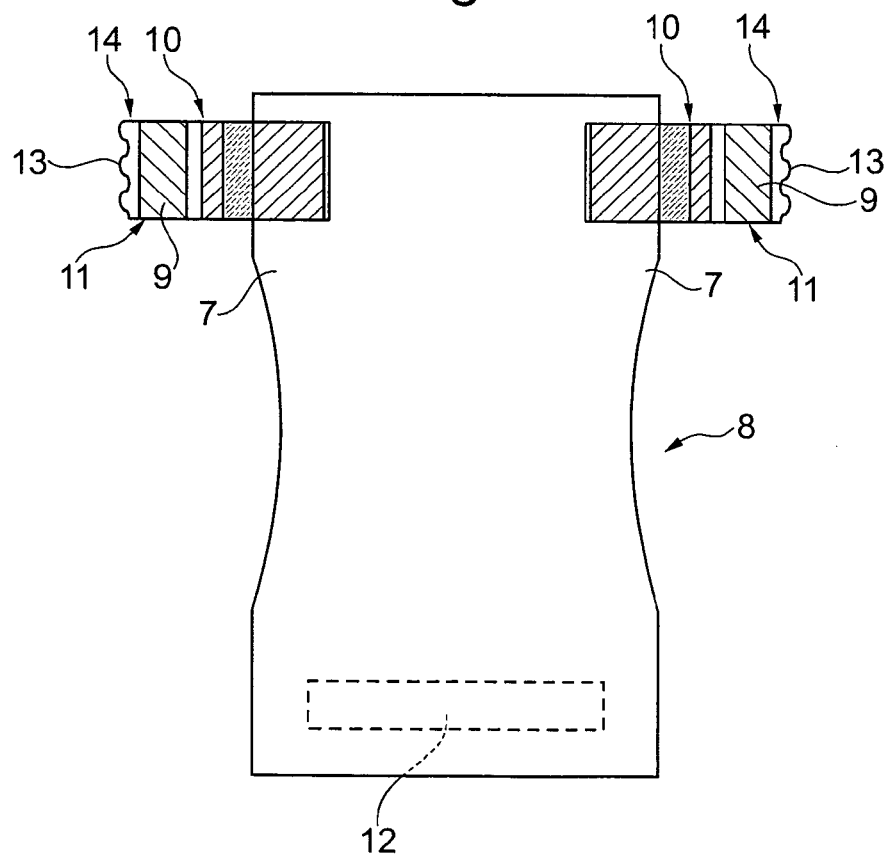

The diaper fastening tapes 10 are attached to the diaper wings 7 (shown as an example in FIGS. 4 and 5) of the diaper 8 so that they can securely seal the diaper 8 by means of hooks 9 on a closing area 11 so that it can be reopened. To this end in these exemplary embodiments, loops corresponding to the hooks 9 are provided on a frontal tape 12 on an outside 17 of the diaper.

A protruding area 14 is provided on the user end 13 for gripping the user end 13 of the diaper fastening tape 10. This directly borders the closing area 11, which is provided with hooks 9 and extends from there in wavy-head-shaped straps 15 of the diaper fastening tape 10 to a tape edge 16 at the end.

In addition to the closing areas 11 of the respective fastening tapes 10, structurally independent components 100 on the protruding sections 14 are elevated away from the remainder of the tape and thus form separate film-like grip areas 24 which embody the present invention. In their precise form and number, the components 100 are subject to few restrictions.

For example, structurally independent components 100, 22, 31, 42, 54, 55 forming different separate film-like grip areas 24, each having a macroscopically structured surface, are provided on the protruding sections in the exemplary embodiments illustrated in FIGS. 6a, 6b, 6c and 6d.

The wavy-head-shaped tip of the protruding section 14 of the first exemplary embodiment 20 in FIG. 6a is free of closing means. The closing area of the fastening tape, a detail of which is shown in the figure, is situated so that it is offset in the direction 21 in relation to the fastening end of the fastening tape outside of the area depicted here. A film 22 approximately 400 µm thick is laminated onto the wavy-head-shaped area 15 of the protruding section 14. The film 22 has numerous macroscopic perforation spots 23 which interrupt the otherwise macroscopically smooth surface of the film 22. The perforation spots 23 are uniformly arranged in a grid pattern which is arranged so it is rotated by 45° with respect to the main direction 21 of the extent of the diaper fastening tape.

The perforation spots 23 provide a macroscopic surface structure to the film 22, imparting a high grip traction to this part of the protruding section 14. Therefore, the film 22 which is perforated at the surface serves as a separate grip area 24. The grip area 24 extends to the edge 16 of the tape, resulting in a grip edge 25 that is easy to grip on the tape edge 16.

It should be pointed out that the plurality of perforations 23 may also be arranged in a different pattern or no pattern at all. There are hardly any limits here to possible options. For example, the spots could also be in an alternative pattern forming concentric rings, triangles, squares or rectangles or may be introduced into the film in a geometric-like curve to the edge 16 of the tape. Instead of perforation spots 23, perforated stars, crosses, lines, triangles, squares, ovals or other shapes may also be selected.

The second embodiment 30 in FIG. 6b (where the detail is selected according to that in FIG. 6a) has a wavy film 31 applied to the tape edge 16 of the wavy-head-shaped area 15 of the protruding section 14. The film 31 is a strip approximately 5 mm wide running directly along the edge 16 of the tape over its entire length. This also yields a grip edge 32 that is easy to grip on the diaper fastening tape. Along the meandering course of the film strip 31 in the surface of the fastening tape, the latter has wavy forms protruding out of the plane of the tape, resulting in numerous ridges 33 running essentially parallel to their neighbors (characterized as an example) being elevated so that the fingers of the user touch these ridges 33 first when gripping the protruding section 14 and therefore are able to grip it well. The strip-shaped film 31 is secured on the diaper fastening tape in the valleys 34 (characterized as an example).

Figure 6C:
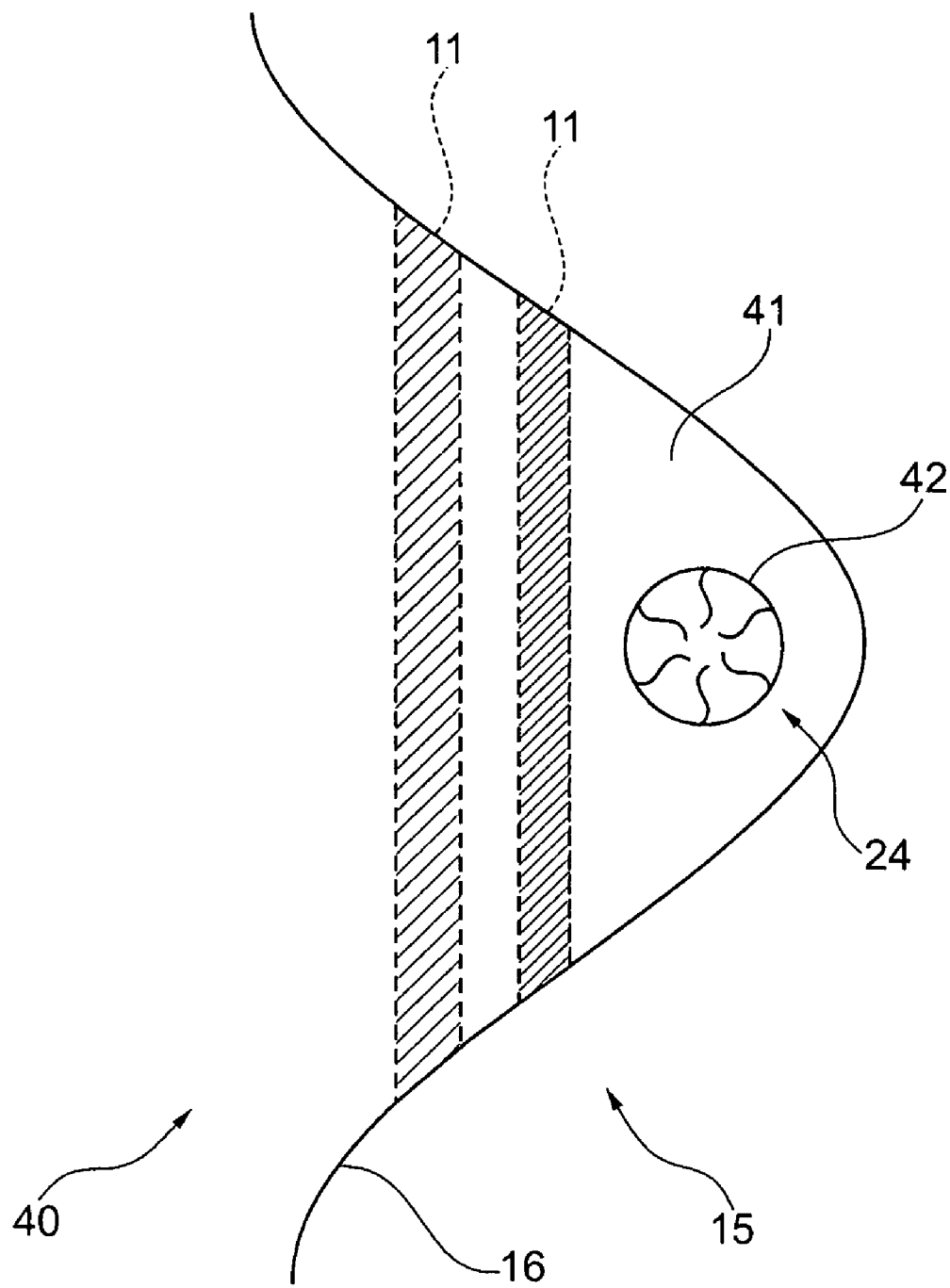

The third exemplary embodiment 40 in FIG. 6c has a closing area 11 that is divided into two strips on its wavy-head-shaped strap 15, resulting in a smaller protruding section 41 at the tip of the strap 15. A circular film spot 42 is laminated onto the fastening tape approximately centered in the protruding section 41. The film spot 42 is embossed with radially arranged strips on its surface. The film 42 of the grip area is approximately 300 µm thick and is arranged on the opposite side of the closing areas 11. In a conventional arrangement of such a diaper fastening tape on a traditional diaper, such that the closing area points toward the inside of the applied diaper, the film spot 42 consequently comes to lie on the outside of the diaper.

Another separate film having a macroscopically structured surface may also be provided on the inside, i.e., on the side of the fastening tape on which the closing areas 11 are also arranged, e.g., to coincide with the circular film spots 42 and be arranged exactly beneath the latter (covered by the film spots 42 in FIG. 6c). Of course other numbers, different geometries or positions may also be used in almost unlimited possible variations for the film spots 42 and also for any spots lying on the other sides.

The fourth exemplary embodiment 50 in FIG. 6d has a strip-shaped closing area 11 with hook material on the inside of the diaper fastening tape on a first wavy head-shaped section 51 and a second wavy head-shaped section 52. To this extent, a protruding section 53 is bordered on the free protruding edge next to the closing areas 11. The diaper fastening tape of the fourth exemplary embodiment 50 has two wavy head-shaped areas 15 on the user end where the closing areas 11 are each positioned identically. Accordingly, the protruding sections 53 are also identical in size and shape.

Figure 6E:
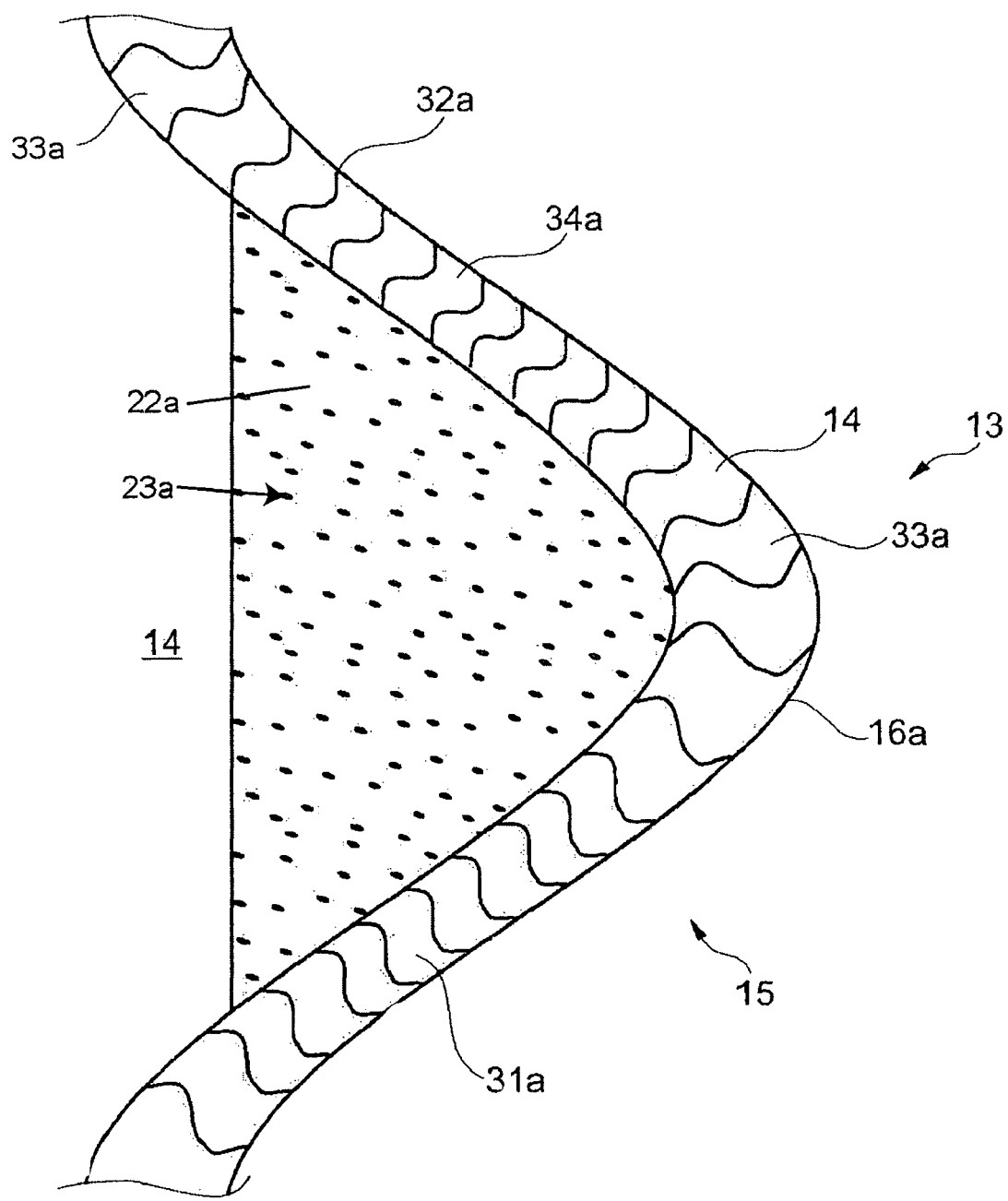

FIG. 6e shows two separate film-like grip areas 22a, 31a having different macroscopically structured surfaces formed by perforation spots 23a in grip area 22a and by ridges 33a in grip area 31a arranged on a grip edge 32a of the protruding section 14. FIG. 6e also shows tape end 16a and valleys 34a between ridges 34a.

A first film 54 and/or a second film 55 are laminated onto the protruding sections 53 and are arranged at the edge 16 of the tape to coincide with this edge and are shaped along an inner edge 56 to be parallel to the borders of the respective closing areas 11. The two films 54, 55 are each approximately 600 μm thick and are provided with embossing (not shown on the film 55). The embossing of the film 54 includes numerous straight and curved lines, grouped together in groups of several lines, forming alphabet letters in the present example. The individual groups, i.e., the letters in the present example, are arranged so they are approximately similar geometrically to the edge 16 of the tape, thereby resulting in a definitely perceptible gripping edge outside of the letters due to an unembossed edge area 57 of the film 54.

As shown on the basis of FIG. 1 in particular, the diaper fastening tape according to the present invention is preferably formed from several layers that are joined together. The diaper fastening tape according to FIG. 1, presented here as an example, has a backing film 80 which in turn has adhesive strips 81 in a fastening area for fastening to a release tape 82, whereby the release tape 82 in turn has an adhesive strip 83 for fastening a diaper. On the other hand, the backing film has an intermediate backing film 84 in a closing area 11 by means of an adhesive strip 85 which in turn carries the hook material 9 as well as the component 100 by means of an adhesive strip 86. As is immediately apparent, the component 100 is thus designed as a separate structural component and is of a different type of material than closing area 11 with hook material 9, and may thus function as a separate grip area 24, since the arrangement according to FIG. 1 has been designed through appropriate separation processes to form diaper fastening tapes that can be applied to a diaper. For the sake of thoroughness, it should also be pointed out that the backing tape 80 has an elastic tape 87, e.g., made of TPE, in an intermediate area and can be slotted in the area of the tape. In this way, the backing tape is elastically stretchable in its intermediate area. It is self-evident that in an alternative embodiment, the backing film 80 and/or the intermediate backing film 84 may also be designed as a grip area, for example, by omitting the separate structural component 100 as well as the area of the adhesive strip 86 beneath that, optionally also the area of the intermediate backing film 84 beneath that and the corresponding area of the adhesive strip 85 and instead providing backing film 80 and/or the intermediate backing film 84 with a macroscopically structured surface. In this way a separate grip area is created because this is formed structurally from a different type of material than the neighboring functional structural component, namely the closing area 11 which is still formed by the hook material having the hooks.

It should be pointed out again that the present invention is not exhausted in the embodiments presented as examples. Even the different types of individual grip areas show that the invention can be implemented in a variety of ways. In particular, grip areas may be provided on only one side of a protruding section or on both sides. When grip areas are provided on both sides, they may be subject to numerous variations in terms of number, position and shape, e.g., in the form of any combinations of the grip areas in question.

The invention claimed is:

1. A fastening tape for a hygiene item having a fastening area for permanent fastening on the hygiene item and having a closing area for simultaneous detachable joining to a hygiene item surface of the hygiene item, said closing area comprising first structural components of a first material, whereby the fastening tape has a protruding section between the closing area and a tape end adjacent to the closing area, wherein the protruding section has a separate film-like grip area having a surface with a macroscopic structure comprising second structural components materially different from said first structural components, said grip area being formed structurally from a different material than the closing area formed by the first material of the first structural components.

2. The fastening tape according to claim 1, wherein the macroscopic structure is a film having a thickness of more than 100 μm.

3. The fastening tape according to claim 1, wherein the surface of the separate grip area has embossing.

4. The fastening tape according to claim 3, wherein the embossing has a plurality of straight and/or curved lines, some of which are joined together.

5. The fastening tape according to claim 1, wherein the grip area is arranged on a grip edge of the protruding section.

6. The fastening tape according to claim 1, wherein the grip area is arranged with an offset to the tape end.

7. The fastening tape according to claim 1, wherein the grip area is designed in strips and runs, at least in part, essentially along a grip edge and/or the tape end in its shape.

8. The fastening tape according to claim 1, wherein the grip area runs in a meandering pattern.

9. The fastening tape according to claim 1, wherein the grip area is approximately the same distance from the closing area as from the tape end.

10. The fastening tape according to claim 1, wherein the grip area is only on an inside of the fastening tape.

11. The fastening tape according to claim 1, wherein the grip area is only on an outside of the fastening tape.

12. The fastening tape according to claim 1, wherein the grip area comprises a common grip area on both sides of the fastening tape or separate grip areas are provided on each side of the fastening tape.

13. The fastening tape according to claim 1, comprising two identically shaped and sized grip areas on both sides of the fastening tape.

14. The fastening tape according to claim 1, comprising two separate film-like grip areas having surfaces with different macroscopic structures.

15. The fastening tape according to claim 1 wherein the closing area comprises a plurality of hooks.

16. A hygiene item comprising a diaper and a diaper fastening tape, the diaper comprising a diaper surface and the diaper fastening tape comprising a fastening area for permanent fastening on the diaper, a closing area for simultaneous detachable joining to the diaper surface comprising first structural components of a first material, and a tape end adjacent to the closing area, wherein the fastening tape has a protruding section between the closing area and the tape end and the protruding section has a separate film-like grip area having a surface with a macroscopic structure comprising second structural components materially different from said first structural components, said grip area being formed structurally from a different material than the closing area formed by the first material of the first structural components.

17. The hygiene item according to claim 16, wherein the closing area comprises a plurality of hooks and the hygiene item further comprises a frontal tape on an outside surface of the hygiene item, said frontal tape comprising a plurality of loops corresponding to the hooks, said hooks and loops forming a two component fastening system.

* * * * *